US011819215B2

(12) United States Patent
Aguilar et al.

(10) Patent No.: US 11,819,215 B2
(45) Date of Patent: Nov. 21, 2023

(54) EMBOLIC DEVICE WITH IMPROVED NECK COVERAGE

(71) Applicant: INCUMEDx, Inc., Fremont, CA (US)

(72) Inventors: Amiel R. Aguilar, San Jose, CA (US); Crystal K. Sein-Lwin, Hayward, CA (US); Nga Doan, San Jose, CA (US); Regina C. Velasco, Fremont, CA (US)

(73) Assignee: INCUMEDx Inc., Newark, CA (US)

( * ) Notice: Subject to any disclaimer, the term of this patent is extended or adjusted under 35 U.S.C. 154(b) by 106 days.

(21) Appl. No.: 16/375,516

(22) Filed: Apr. 4, 2019

(65) Prior Publication Data

US 2019/0307546 A1   Oct. 10, 2019

Related U.S. Application Data

(60) Provisional application No. 62/652,441, filed on Apr. 4, 2018.

(51) Int. Cl.
*A61B 17/12* (2006.01)
*A61M 25/06* (2006.01)
(Continued)

(52) U.S. Cl.
CPC .. *A61B 17/12145* (2013.01); *A61B 17/12022* (2013.01); *A61B 17/12031* (2013.01);
(Continued)

(58) Field of Classification Search
CPC ........ A61B 17/12031; A61B 17/12113; A61B 17/12145; A61B 17/12154;
(Continued)

(56) References Cited

U.S. PATENT DOCUMENTS 5,769,884 A   6/1998 Solovay
5,853,418 A   12/1998 Ken et al.
(Continued)

FOREIGN PATENT DOCUMENTS

CN   203885667 U   10/2014
CN   106491174 A   3/2017
(Continued)

OTHER PUBLICATIONS

Invitation to Pay Additional fees issued for PCT/US2019/025770, dated Jul. 22, 2019.
(Continued)

*Primary Examiner* — Shaun L David
(74) *Attorney, Agent, or Firm* — Goodwin Procter LLP

(57) ABSTRACT

In various aspects, the invention relates to an embolic device for treating aneurysms or other vascular disorders that exhibits improved filling and/or neck blockage over conventional devices. As one example, the embolic device can include a structure that is wound into a spiral shape. In some cases, the spirally wound embolic device includes alternating narrow portions and link portions. As another example, the embolic device can be formed from a structure wound to form an infinity shape or, in some cases, multiple infinity shapes. In instances with multiple infinity shapes, the infinity shapes can be arranged either parallel or perpendicular to each other. In certain aspects, the embolic device can include two different embolic devices that are attached by an interconnect element, such that the two devices are attached but have independent freedom of motion when placed within a vascular disorder.

12 Claims, 12 Drawing Sheets

(51) Int. Cl.
*A61F 2/01* (2006.01)
*A61M 25/10* (2013.01)
*A61B 17/00* (2006.01)

(52) U.S. Cl.
CPC .. *A61B 17/12113* (2013.01); *A61B 17/12154* (2013.01); *A61B 17/12163* (2013.01); *A61B 17/12172* (2013.01); *A61B 2017/00632* (2013.01); *A61B 2017/00778* (2013.01); *A61B 2017/00867* (2013.01); *A61B 2017/1205* (2013.01); *A61F 2/011* (2020.05); *A61F 2002/016* (2013.01); *A61F 2002/018* (2013.01); *A61F 2250/0059* (2013.01); *A61M 2025/0681* (2013.01); *A61M 2025/1047* (2013.01)

(58) Field of Classification Search
CPC ........ A61B 17/12163; A61B 17/12172; A61B 17/1214; A61F 2/013
See application file for complete search history.

(56) References Cited

U.S. PATENT DOCUMENTS

| | | | |
|---|---|---|---|
| 5,935,148 A * | 8/1999 | Villar | A61B 17/12113 606/213 |
| 6,258,115 B1 | 7/2001 | Dubrul | |
| 6,416,530 B2 | 7/2002 | DeVries et al. | |
| 6,602,261 B2 | 8/2003 | Greene, Jr. et al. | |
| 7,763,011 B2 | 7/2010 | Ortiz et al. | |
| 7,875,044 B2 | 1/2011 | Feller, III et al. | |
| 8,388,650 B2 | 3/2013 | Gerberding et al. | |
| 8,425,548 B2 | 4/2013 | Connor | |
| 8,974,488 B2 | 3/2015 | Tan et al. | |
| 9,192,491 B1 | 11/2015 | Raju et al. | |
| 9,277,924 B2 | 3/2016 | Clarke et al. | |
| 9,339,367 B2 | 5/2016 | Carpenter et al. | |
| 9,358,140 B1 | 6/2016 | Connor et al. | |
| 9,433,518 B2 | 9/2016 | Rudakov et al. | |
| 9,517,146 B2 | 12/2016 | Fierens et al. | |
| 9,636,117 B2 | 5/2017 | Bachman et al. | |
| 9,675,476 B2 | 6/2017 | Berez et al. | |
| 9,795,389 B2 | 10/2017 | Elliott | |
| 9,814,465 B2 | 11/2017 | Win et al. | |
| 2002/0087077 A1* | 7/2002 | Wallace | A61B 17/12113 600/434 |
| 2002/0120276 A1* | 8/2002 | Greene, Jr. | A61B 17/12145 606/108 |
| 2002/0177855 A1 | 11/2002 | Greene et al. | |
| 2003/0051735 A1 | 3/2003 | Pavcnik et al. | |
| 2003/0065354 A1 | 4/2003 | Boyle et al. | |
| 2003/0109917 A1 | 6/2003 | Rudin et al. | |
| 2003/0199887 A1 | 10/2003 | Ferrera et al. | |
| 2005/0267510 A1* | 12/2005 | Razack | A61B 17/12172 606/200 |
| 2005/0283220 A1 | 12/2005 | Gobran et al. | |
| 2006/0135986 A1* | 6/2006 | Wallace | A61B 17/12154 606/200 |
| 2006/0271097 A1 | 11/2006 | Ramzipoor et al. | |
| 2006/0271098 A1 | 11/2006 | Peacock | |
| 2006/0276831 A1 | 12/2006 | Porter et al. | |
| 2006/0281966 A1 | 12/2006 | Peacock | |
| 2007/0016283 A1 | 1/2007 | Greenhalgh et al. | |
| 2007/0021816 A1 | 1/2007 | Rudin | |
| 2007/0142859 A1 | 6/2007 | Buiser et al. | |
| 2007/0219619 A1 | 9/2007 | Dieck et al. | |
| 2008/0147111 A1* | 6/2008 | Johnson | A61F 2/01 606/200 |
| 2008/0281350 A1 | 11/2008 | Sepetka et al. | |
| 2009/0112251 A1* | 4/2009 | Qian | A61B 17/12163 606/194 |
| 2011/0054515 A1 | 3/2011 | Bridgeman et al. | |
| 2012/0158034 A1* | 6/2012 | Wilson | A61B 17/1214 606/192 |
| 2012/0245614 A1* | 9/2012 | Drasler | A61B 17/12172 606/191 |
| 2013/0123901 A1 | 5/2013 | Connor et al. | |
| 2014/0114343 A1 | 4/2014 | Lee et al. | |
| 2014/0303667 A1 | 10/2014 | Cox et al. | |
| 2014/0336741 A1 | 11/2014 | Connor et al. | |
| 2014/0371777 A1 | 12/2014 | Rudakov et al. | |
| 2015/0010581 A1 | 1/2015 | Lewis | |
| 2015/0039015 A1 | 2/2015 | Gerberding | |
| 2015/0374382 A1 | 12/2015 | Lorenzo | |
| 2016/0032503 A1 | 2/2016 | Lorenzo | |
| 2016/0120551 A1* | 5/2016 | Connor | A61B 17/12177 606/200 |
| 2016/0151141 A1 | 6/2016 | Zimmerman | |
| 2016/0199204 A1 | 7/2016 | Pung et al. | |
| 2016/0374690 A9 | 12/2016 | Connor | |
| 2017/0020532 A1 | 1/2017 | Islak et al. | |
| 2017/0042551 A1 | 2/2017 | Celermajer et al. | |
| 2017/0079661 A1 | 3/2017 | Bardsley et al. | |
| 2017/0224350 A1* | 8/2017 | Shimizu | A61B 17/1214 |
| 2017/0252044 A1 | 9/2017 | Elgaard et al. | |
| 2017/0319214 A1 | 11/2017 | Rudakov | |
| 2017/0367708 A1 | 12/2017 | Mayer et al. | |
| 2018/0049859 A1* | 2/2018 | Stoppenhagen | A61F 2/01 |

FOREIGN PATENT DOCUMENTS

| | | |
|---|---|---|
| DE | 102010027106 A1 | 1/2012 |
| KR | 101300437 B1 | 8/2013 |
| WO | WO-01/93920 A2 | 12/2001 |
| WO | WO-2009/014528 A1 | 1/2009 |
| WO | WO-2011057277 A2 | 5/2011 |
| WO | WO-2016/108241 A1 | 7/2016 |
| WO | WO 2017221252 A1 * | 12/2016 |
| WO | WO-2017/106567 A1 | 6/2017 |
| WO | WO-2017/221252 A1 | 12/2017 |

OTHER PUBLICATIONS

Sourour NA, et al. "Medina® Embolization Device for the Treatment of Intracranial Aneurysms: Safety and Angiographic Effectiveness at 6 Months." *Neurosurgery*, Feb. 1, 2018;82(2):155-162.
Healthcare Professionals, Pipeline Flex Embolization Device, Aneurysm Flow Diversion, accessed on Apr. 17, 2019.
Maksim Shapiro, "Pipeline Embolization Device and Treatment of Brain Aneurysms", neuroangio.org, accessed on Apr. 17, 2019.
Instructions for Use (IFU), Pipeline Embolization Device, drafted on Apr. 4, 2011.
International Search Report and Written Opinion issued for PCT/US2019/025770, dated Oct. 24, 2019.

* cited by examiner

EMBOLIC DEVICE WITH IMPROVED NECK COVERAGE

CROSS-REFERENCE TO RELATED APPLICATION

This application claims priority to and the benefit of, and incorporates herein by reference in its entirety, U.S. Provisional Patent Application No. 62/652,441, which was filed on Apr. 4, 2018.

TECHNICAL FIELD

In general, various embodiments of this invention relate to embolic devices for use in the minimally-invasive treatment of aneurysms and other vascular disorders and, more specifically, to an embolic device that can be shaped and/or configured to accomplish improved filling and/or coverage of a neck of a vascular disorder.

BACKGROUND

In general, an aneurysm is a swelling or bulge that forms a cavity in the wall of a blood vessel. One type of aneurysm is a cerebral aneurysm, which forms in an artery of the brain. A cerebral aneurysm may develop suddenly without initial symptoms, and can cause extreme pain. In general, in 15% of cerebral aneurysm cases, the patient dies suddenly upon development of the cerebral aneurysm; in another 15% of cerebral aneurysm cases, the patient dies under medical treatment; and in 30% of cerebral aneurysm cases, the patient survives after treatment but feels an acute aftereffect. As such, a cerebral aneurysm (or any aneurysm) is a very concerning development.

The treatment of aneurysms and other similar vascular disorders often involves the placement of microcoils within the cavity formed by the aneurysm or disorder. Doing so can cause blood to clot, prevent an additional inflow of blood, and decrease the risk of the aneurysm or disorder rupturing (i.e., an embolization). In order to be effective, an embolic microcoil must apply pressure sufficient to prevent additional inflow of blood, but not an excessive amount of pressure that causes rupture.

An important feature of an embolic device is its ability to block the aneurysm's neck, i.e., the opening where the aneurysm meets the blood vessel. Such blockage can be critical for ensuring that excessive amounts of blood do not flow into the aneurysm, risking further bulging or rupture. Prior approaches for blocking the aneurysm neck include covering the neck with stent-like or braided structures. While these approaches can sometimes be effective, there are still opportunities for improvement.

Accordingly, there is a need for an improved embolic device that achieves improved filling and/or blockage of a neck of an aneurysm.

SUMMARY OF THE INVENTION

In various embodiments, the present invention relates to an improved embolic device that achieves improved filling and neck blockage over conventional devices. In particular, the device can be formed into inventive shapes that have been observed to improve neck blockage. Exemplary shapes include spiral shapes and infinity shapes, as described in greater detail below.

In addition, one factor that has been discovered to contribute significantly to unsatisfactory neck blockage in conventional devices is that the portion of the embolic device placed within the aneurysm often shifts or moves while it finds equilibrium within the aneurysm. This can take place, for example, when the aneurysm has a complex shape (e.g., bifurcated, bilobed, etc.) and the portion of the embolic device within the aneurysm expands in order to contact portions of the interior surface of the aneurysm. Movement of the portion of the device within the aneurysm can cause associated shifts/movement of the portion of the embolic device blocking the neck, which can compromise the blockage. As such, in some aspects, the invention described herein includes an embolic device that includes two treatment elements: one for placement in the aneurysm and the other for blockage of the neck. The two treatment elements can be attached with an interconnect element that allows the treatment elements to have independent freedom of motion when delivered to the aneurysm.

In general, in one aspect, embodiments of the invention feature an embolic device for use in treating a vascular disorder. The embolic device can include a flexible structure that includes a series of alternating narrow portions and link portions, each link portion circumscribing an opening in at least one plane. The structure can be adapted to form a spiral shape when unconstrained.

In various embodiments, the structure can include a coil, a flat sheet, a thin film, and/or combinations thereof. The structure can include a material including platinum, nitinol, alloys thereof, and/or combinations thereof. In some cases, the structure includes a thickness in a range from 0.0005 inches to 0.027 inches. In some cases, each narrow portion includes a helically wound coil and each link portion includes a flat sheet and/or a thin film. At least a portion of the embolic device can be radiopaque. Each narrow portion can be fixedly attached to proximate link portions. In some cases, the embolic device can include a strain relief element (e.g, a melted suture material, melted polymer, etc.) between each narrow portion and the proximate link portions. In some cases, each link portion includes a diamond-like shape.

In various embodiments, each link portion is adapted to compress when the embolic device is disposed within a microcatheter. Each link portion can be further adapted to expand upon deployment of the embolic device from the microcatheter. In some cases, the narrow portions and the link portions alternate with consistent spacing. In other cases, the narrow portions and the link portion alternate with inconsistent spacing. The embolic device can include a cover element disposed over the structure. The embolic device can include an interconnect element disposed at an end of the embolic device for attaching the embolic device to one or more different embolic devices (e.g., in series).

In general, in another aspect, embodiments of the invention feature another embolic device for use in treating a vascular disorder. The embolic device can include a flexible structure adapted to form at least one infinity shape portion when unconstrained. The infinity shape portion can include two adjacent loops crossing at a single point.

In various embodiments, the structure includes a coil, a flat sheet, a thin film, and/or combinations thereof. The structure can include a material that includes platinum, nitinol, alloys thereof, and/or combinations thereof. In some instances, the structure includes a thickness in a range from 0.0005 inches to 0.027 inches. In some cases, the flexible structure forms at least two infinity shape portions. At least two of the infinity shape portions can be arranged to align with and overlay each other and/or at least two infinity shape portions can be arranged circumferentially about an interior of the vascular disorder. At least one infinity shape portion can be rotated to be perpendicular to another infinity shape portion. The embolic device can include a cover element disposed over the structure. The embolic device can include an interconnect element disposed at an end of the embolic device for attaching the embolic device to one or more different embolic devices (e.g., in series).

In general, in yet another aspect, embodiments of the invention feature a multi-stage embolic device for use in treating a vascular disorder. The multi-stage embolic device can include a first embolic device, a second embolic device different from the first embolic device, and an interconnect element joining the first and second embolic devices and permitting independent freedom of motion between the first and second embolic devices while remaining joined together.

In various embodiments, the first embolic device includes a framing device and the second embolic device includes a filling device. In some cases, upon deployment of the multi-stage embolic device to the vascular disorder, the first embolic device is adapted to block a neck of the vascular disorder and the second embolic device is adapted to occupy an interior of the vascular disorder. The first and/or second embolic devices can include a coil, a flat sheet, a thin film, and/or combinations thereof. The first and/or second embolic devices can include platinum, nitinol, alloys thereof, and/or combinations thereof. In some instances, the first and/or second embolic devices include a thickness in a range from 0.0005 inches to 0.027 inches. In some cases, the first and/or second embolic devices are adapted to form a spiral shape when unconstrained. The interconnect element can include linked loops and/or a nitinol coil. The multi-stage embolic device can further include at least one additional embolic device different from each of the first and second embolic devices, and at least one additional interconnect element directly and/or indirectly joining the second and additional embolic device(s). The additional interconnect element(s) permit independent freedom of motion between the second and additional embolic device(s) while remaining joined together. The multi-stage embolic device can include a cover element disposed over the first and/or second embolic devices.

In general, in still another aspect, embodiments of the invention feature a method for treating a vascular disorder. The method can include the step of delivering a multi-stage embolic device to the vascular disorder. The multi-stage embolic device may include a first embolic device, a second embolic device different from the first embolic device, and an interconnect element joining the first and second embolic devices and permitting independent freedom of motion between the first and second embolic devices while remaining joined together. The method can further include disposing the second embolic device within an interior of the vascular disorder, and disposing the first embolic device to block a neck of the vascular disorder.

In various embodiments, one of the first and second embolic devices includes a framing device and the other embolic device includes a filling device. The first and/or second embolic devices can include a coil, a flat sheet, a thin film, and/or combinations thereof. The first and/or second embolic devices can include platinum, nitinol, alloys thereof, and/or combinations thereof. In some instances, the first and/or second embolic devices include a thickness in a range from 0.0005 inches to 0.027 inches. In some cases, the first and/or second embolic devices form a spiral shape when unconstrained. The interconnect element can include linked loops and/or a nitinol coil. The multi-stage embolic device can further include at least one additional embolic device different from each of the first and second embolic devices, and at least one additional interconnect element directly and/or indirectly joining the second and additional embolic devices. The additional interconnect element(s) permit independent freedom of motion between the second and additional embolic devices while remaining joined together, and the method can further include disposing the additional embolic device(s) within the interior of the vascular disorder. The multi-stage embolic device can include a cover element disposed over the first and/or second embolic devices.

These and other objects, along with advantages and features of the embodiments of the present invention herein disclosed, will become more apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which.

DESCRIPTION

Figure 1:
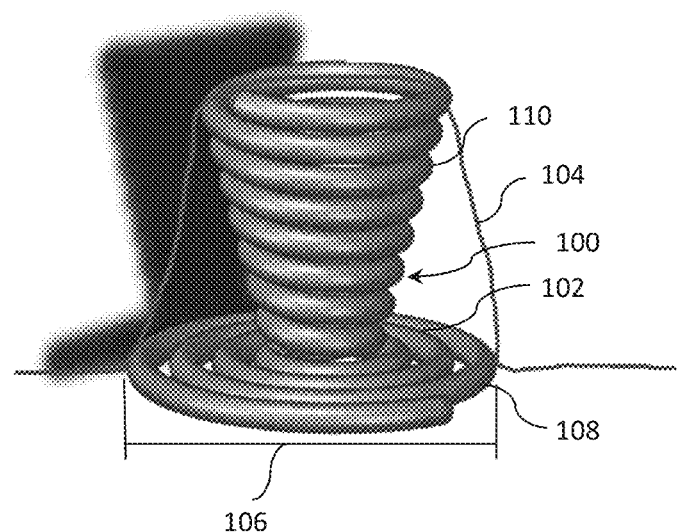
FIG. 1 is schematic perspective view of an embolic device having a spiral shape disposed within an aneurysm, according to one embodiment of the invention.

Embodiments of the present invention are directed toward an improved design for an embolic device and methods of using the improved device. Neck blockage is an important function for embolic devices because it determines how much fluid can pass through the embolic device into the aneurysm, which can directly impact how effective the embolic device is in treating the vascular disorder. Embodiments of the present invention include embolic devices having shapes and/or configurations that accomplish improved neck blockage and other performance parameters over conventional devices.

In general, all of the embolic devices described herein can take any known form, e.g., a microcoil (e.g., bare platinum coil), flat sheet, thin film, combinations thereof, etc., even though in some instances a particular device may only be described herein as having one of these forms. In addition, all of the embolic devices described herein can be formed from any suitable material, e.g., shape memory material (e.g., nitinol), platinum, combinations thereof, etc., even though in some instances a particular device may only be described herein as being formed of one of these materials. Furthermore, in various instances, all of the embolic devices described herein can include a structure (e.g., microcoil, flat sheet, thin film, etc.) covered by a cover element, as described for example in U.S. Patent Publication No. US-2016-0022275-A1, which is incorporated herein by reference in its entirety.

In various embodiments of the invention, an embolic device is formed from a structure. As shown for example in FIG. 1, the embolic device 100 may be adapted to form a spiral shape upon deployment to an aneurysm 104 (reference numeral 104 can also apply to any other vascular disorder or similar anatomic structure). As used herein, the shape of the embolic device 100 refers to a macro shape formed by the embolic device 100 itself (or a portion thereof), as opposed to a micro shape used to form the structure 102. For example, in some instances, the embolic device 100 includes a structure 102 that is formed from a spirally wound wire 200, as shown in FIG. 2. In the example of FIG. 2, although the structure 102 is spirally wound, the macro shape into which it is formed to create the embolic device is not spirally wound, instead forming a series of curved, lobe-shaped loops. Thus, when the shape of the embolic device 100 is described herein it should be understood as having this macro shape meaning.

Figure 2:
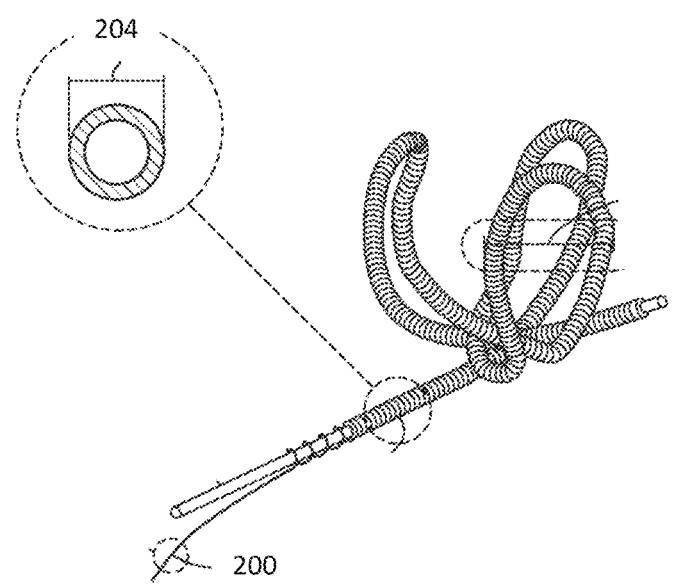
FIG. 2 is a schematic perspective view of a coil formed from a spirally wound wire used in various embodiments of the invention.

As shown in FIG. 1, the embolic device 100 can be used to treat a vascular disorder 104 that has a neck 106, e.g., an opening between a blood vessel and a cavity of the aneurysm 104. In some instances, the embolic device 100 can include a portion 108 disposed within and/or blocking the aneurysm neck 106 and another portion 110 disposed within the cavity of the aneurysm 104. In general, the portion 108 blocking the neck 106 can take any shape, e.g., a spiral shape as shown in FIG. 1. The spiral shape of the portion 108 can be formed in any suitable three dimensional shape, e.g., a disc (as shown in FIG. 1), a sphere, a semi-sphere (or partial-sphere), a cone, etc. The portion 108 having a spiral shape has been observed to accomplish improved blockage of the neck 106 over conventional devices. The portion 110 disposed within the cavity of the aneurysm 104 can also take any shape, which can be the same or a different shape as the portion 108 blocking the aneurysm neck 106. For example, as shown in FIG. 1, the portion 110 can have a spiral shape, but in other embodiments it can have other shapes, including random or non-geometric shapes. The spiral of the portion 110 can also be formed in any suitable three-dimensional shape, e.g., a disc, a sphere, a semi-sphere (or partial sphere), a cone (as shown in FIG. 1), etc.

One problem experienced with conventional devices is that their effectiveness in blocking an aneurysm neck is significantly affected by the orientation of the device upon delivery to a treatment site, which can sometimes be difficult to accomplish in a repeatable manner. Embodiments of the present invention solve this problem by featuring an embolic device that effectively blocks the aneurysm neck 106 regardless of its orientation upon placement into the aneurysm 104 or, in some cases, that blocks the aneurysm neck 106 in many more orientations than a conventional device (e.g., the majority of the orientations).

Figure 3:
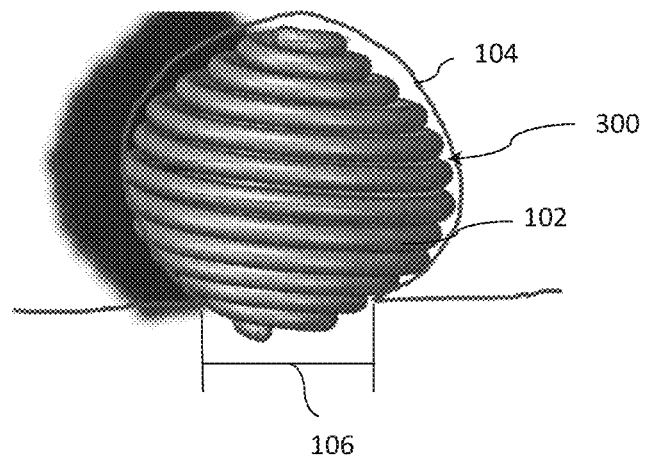
FIG. 3 is a schematic perspective view of an embolic device having a substantially spherical spiral shape, according to one embodiment of the invention.

One example of a device that blocks the aneurysm neck 106 in a majority (or, in some cases, all) orientations is the embolic device 300 shown in FIG. 3, which has a substantially spherical spiral shape. When a geometric shape is described herein, in various embodiments, it includes a shape having all of its dimensions within 35% of a perfect geometric version of the shape, e.g., 25%, 10%, 5%, 2%, and/or 1%. As illustrated in FIG. 3, the embolic device 300 can be deployed into the aneurysm 104 in any 360 degree orientation and still effectively block the neck 106 and also contact the interior wall (endothelium) of the aneurysm. In some instances, the substantially spherical spiral shaped embolic device 300 can allow for continuous growth of tissue throughout the device 300. For example, the embolic device 300 can provide a continuous path for tissue to grow within the aneurysm cavity, which can enable and/or accelerate healing of the aneurysm 104.

Figure 4A:
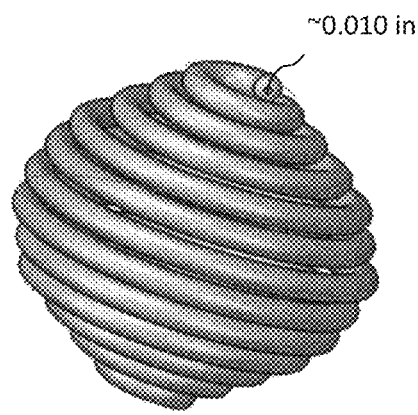
FIG. 4A is a schematic perspective view showing an exemplary dimension of an embolic device having a substantially spherical spiral shape, according to one embodiment of the invention.
Figure 4B:
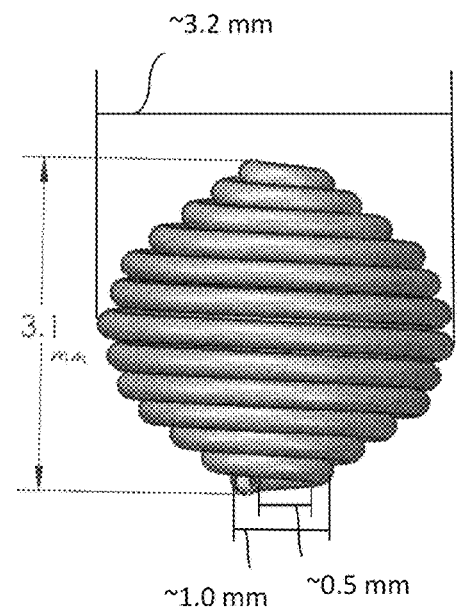
FIG. 4B is a schematic side view showing exemplary dimensions of an embolic device having a substantially spherical spiral shape, according to one embodiment of the invention.
Figure 4C:
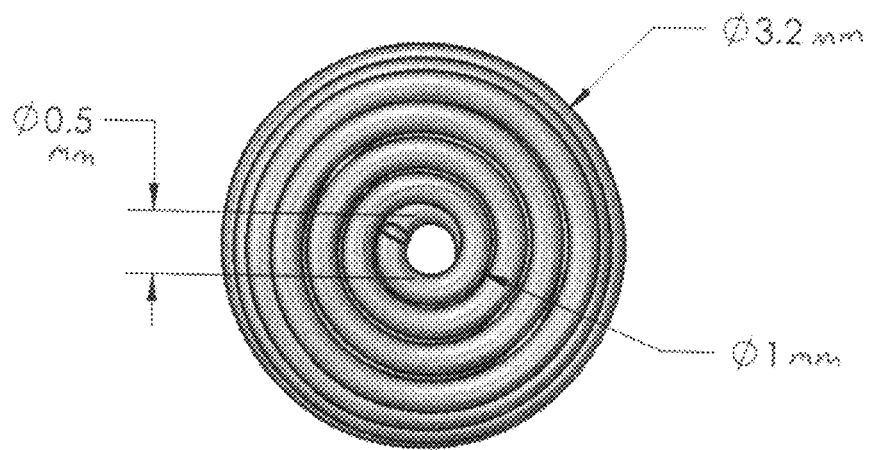
FIG. 4C is a schematic top view showing exemplary dimensions of an embolic device having a substantially spherical spiral shape, according to one embodiment of the invention.

Example dimensions of the embolic device 300 are shown in FIGS. 4A-4C. The primary diameter (see element 204 in FIG. 2) can be about 0.010 inches. The height of the device (distance between top-most coil and bottom-most coil) can be about 3.1 mm. The diameter of the widest portion of the spherical spiral can be about 3.2 mm. The outer diameter of the bottom-most coil can be about 1.0 mm and the inner diameter of the bottom-most coil can be about 0.5 mm. The top-most coil can have similar dimensions to the bottom-most coil.

Figure 5A:
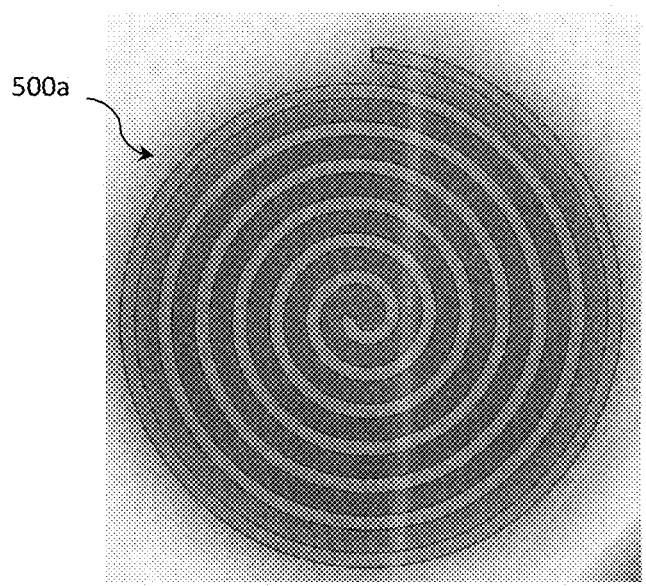
FIG. 5A is a schematic top view of an embolic device formed from a flat sheet of material having a constant width, according to one embodiment of the invention.
Figure 5B:
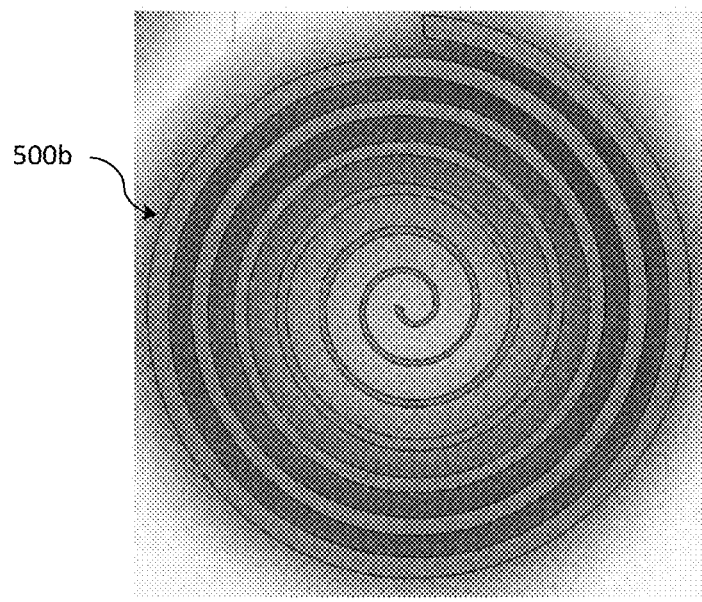
FIG. 5B is a schematic top view of an embolic device formed from a flat sheet of material having a drafted width, according to one embodiment of the invention.

In various embodiments, embolic devices of the present invention can be formed from a flat sheet (e.g., formed from nitinol). In general, the flat sheet can be formed into any suitable shape. For example, FIGS. 5A-5B show top views of example embolic devices 500a, 500b formed from a flat sheet in a spiral shape. As mentioned above, the spirals can take any suitable 3D shape, e.g., disc, sphere, semi-sphere (or partial sphere), cone, etc. The flat sheet can also have any desirable thickness, e.g., in a range from 0.0001" to 0.030", in a range from 0.0005" to 0.027", in a range from 0.001" to 0.025", in a range from 0.002" to 0.020", in a range from 0.003" to 0.015", in a range from 0.004" to 0.010", in a range from 0.006" to 0.008". In another embodiments, the flat sheet has a thickness in a range from 0.002" to 0.004". In some instances, the width of the flat sheet has a constant width, as shown for example by the embolic device 500a in FIG. 5A. In other instances, the width of the flat sheet has a drafted or tapered (e.g., decreasing or increasing) width, as shown for example by the embolic device 500b in FIG. 5B.

Figure 6:
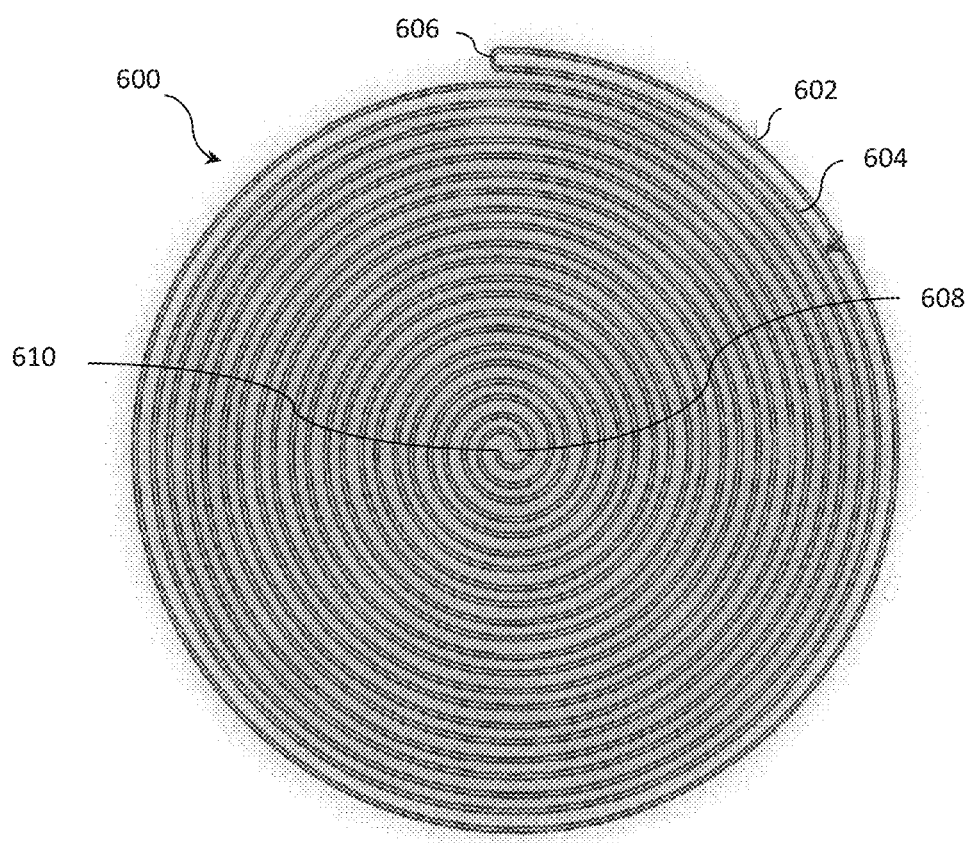
FIG. 6 is a schematic top view of an embolic device formed from two spiral portions connected at a connection region, according to one embodiment of the invention.

In various embodiments, as shown in FIG. 6, an embolic device 600 can be formed by connecting two spiral elements 602, 604 at a connection region 606. In general, the spiral elements 602, 604 can be formed from any suitable structure, e.g., microcoil, flat sheet (as shown in FIG. 6), thin film, etc. In general, the connected spiral elements can form any 3D shape, e.g., disc, sphere, semi-sphere (or partial sphere), cone, etc. With reference to FIG. 6, as one example, if an end point 608 of the first spiral element 602 is pulled out of the page, a cone shaped spiral is formed. As another example, if an end point 610 of the second spiral element 604 is also pushed into the page, a sphere shaped spiral is formed. In general, the spiral elements 602, 604 can be joined at the connection region 606 using any suitable technique, e.g., welding (e.g. laser, arc, resistance, friction stir), soldering, brazing, diffusion bonding, adhesive joining, and interconnect element (e.g., as described below), etc. In other embodiments, both spiral elements 602, 604 can both be cut (e.g., laser cut) from a single piece of material (i.e., the spiral elements 602, 604 are of unitary construction with each other).

Figure 7:
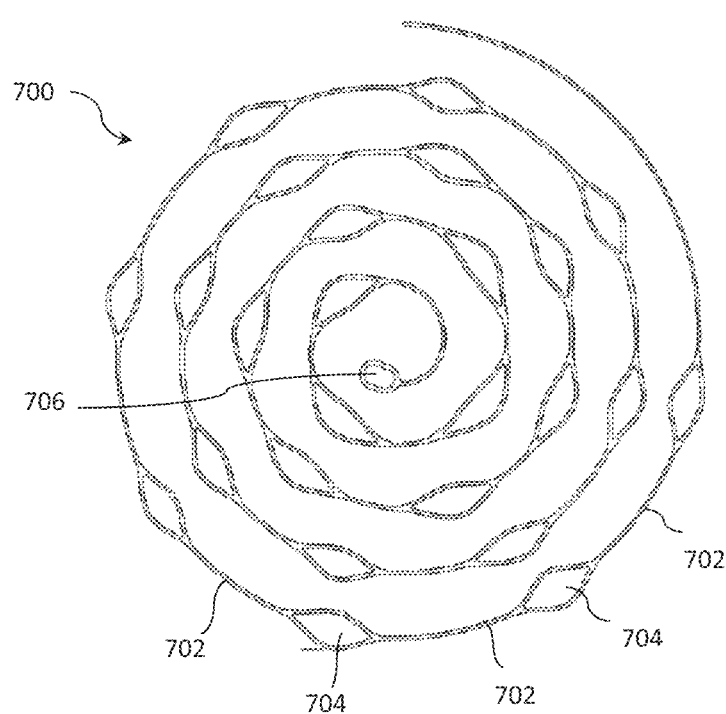
FIG. 7 is a schematic top view of an embolic device having narrow portions and link portions, according to one embodiment of the invention.
Figure 8:
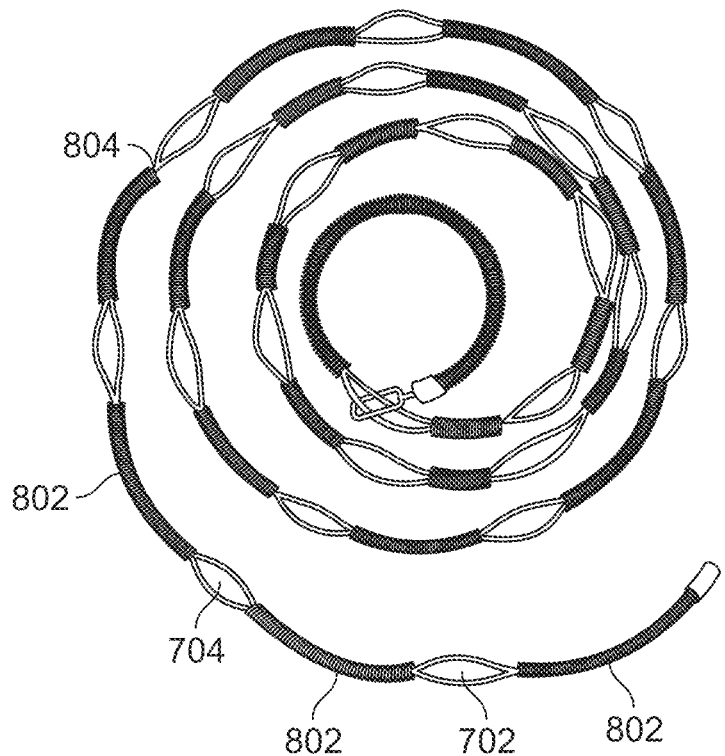
FIG. 8 is a picture of an embolic device having narrow portions, formed from coil segments, and link portions, according to one embodiment of the invention.

In various embodiments, an embolic device 700 can include alternating narrow portions 702 and link portions 704, as shown for example in FIG. 7. The link portions 704 circumscribe an opening in at least one plane, e.g., the plane of the page, as shown in FIG. 7. In general, the link portions 704 can have any suitable shape, e.g., diamond-like (e.g., as shown in FIGS. 7 and 8), circular, rectangular, triangular, etc. In general, the embolic device 700 can be formed from any suitable structure, e.g., a coil, a flat sheet, a thin film, combinations thereof, etc. For example, as shown in FIG. 7, the narrow portions 702 can be formed of a single strip of flat sheet material (or multiple strips of flat sheet material with no opening in between) and the link portions 704 can be formed by at least two strips of flat sheet material that define a perimeter around or circumscribes an opening. The embolic device 700 can also have any desirable thickness, e.g., in a range from 0.0001" to 0.030", in a range from 0.0005" to 0.027", in a range from 0.001" to 0.025", in a range from 0.002" to 0.020", in a range from 0.003" to 0.015", in a range from 0.004" to 0.010", in a range from 0.006" to 0.008". In another embodiment, the embolic device has a thickness in a range from 0.002" to 0.004".

In some instances, as shown for example in FIG. 8, the narrow portions include coil segments 802. In some cases, the coil segments 802 are disposed over another structure (e.g., a flat sheet, thin film, etc.). In other cases, the coil segments 802 are not disposed over another structure. In general, the coil segments 802 can be attached to the link portions 704 using any known technique, e.g., melting a suture on the ends of each coil segment 802. Melting a suture on the ends of each coil segment 802 can also keep the coil segment 802 positioned between the link portions 704. In some instances, the link portions 704 can be fixedly attached to proximate narrow portions and a strain relief element 804 can be used to relieve strain between the portions. The strain relief element can be formed of any suitable material, e.g., a suture material, a melted polymer (e.g., polypropylene, polyethylene, high density polyethylene, low density polyethylene, polyurethane, polyether block amide, polyamides, polymer adhesives, etc.), etc.

In various embodiments, the embolic devices described herein can be introduced, delivered, positioned, and implanted within a vascular disorder using a microcatheter. The microcatheter can be a flexible, small diameter catheter having, for example, an inside diameter between 0.015 inches and 0.035 inches (e.g., between 0.016 inches and 0.021 inches). The microcatheter may be introduced by an introducer sheath/guiding catheter combination placed in the femoral artery or groin area of a patient. In some instances, the microcatheter is guided into the vascular disorder with guidewires (e.g., long, torqueable proximal wire sections with more flexible distal wire sections designed to be advanced within tortuous vessels). Such guidewires may be visible using fluoroscopy and may be used to first access the vascular disorder, thereby allowing the microcatheter to be advanced over it into the disorder.

In some instances, once the tip of the microcatheter has accessed the vascular disorder, the guidewire is removed from the catheter lumen. The embolic device may then be placed into the proximal open end of the microcatheter and advanced through the microcatheter with a delivery mechanism. The embolic device may attach to a delivery mechanism via any suitable structure, e.g., a loop 706 (FIG. 7) on a proximal end of the device. In some instances, while the embolic device is disposed within the lumen of the microcatheter it is in a straightened out form. A user (e.g., a physician) may advance and/or retract the embolic device several times to obtain a desirable position of the embolic device within the disorder. Once the embolic device is satisfactorily positioned, it can be released into the disorder. Upon release, the device may form its deployed shape, for example the spiral shapes described above, or any other desired configuration. In some instances, the formation of the shape upon deployment into the vascular disorder is caused by the shape-memory nature of the material used to form the embolic device (e.g., nitinol).

Further explanation regarding the shape of the embolic devices described herein at various stages of the delivery process is instructive. The embolic device are generally manufactured to have a particular shape in an unconstrained configuration, e.g., as the device would exist in packaging or an operating room before being delivered to a patient. The particular shape can include any of the embolic device shapes described herein. During delivery, the embolic device is straightened out so that it can fit within and be delivered through a microcatheter (as described above). Once deployed out of the microcatheter to the vascular disorder, the embolic device can reform the shape it was manufactured to have (e.g., aided by a shape memory material). However, in some instances, the embolic device may not reform exactly into the shape it was manufactured to have, based on constraints imposed by the vascular disorder and other surrounding structures.

In various embodiments, the link portions 704 of the embolic device 700 shown in FIG. 7 can collapse (e.g., the openings can become narrower) when the embolic device 700 is located in a microcatheter during delivery. The link portions 704 can then expand (e.g., the openings can become wider) upon deployment of the embolic device to the vascular disorder. This can allow the embolic device 700 to be more easily delivered with less friction through a microcatheter, while also effectively blocking the neck of the aneurysm upon deployment. In some instances, the coil segments 802 can further reduce friction of the embolic device during delivery through a microcatheter. As one example, the shape of the coil segments 802 can better match the shape of a lumen of the microcatheter. As another example, the coil segments 802 can increase the flexibility and malleability of the embolic device. As another example, the coil segments 802 can be formed of a material that generates less friction with the interior surface of the microcatheter. The coil segments 802 can also be formed of a radiopaque material (e.g., platinum) such that the embolic device can be viewed during delivery; for example, if the link portions 704 are formed from a non-radiopaque material.

Figure 9A:
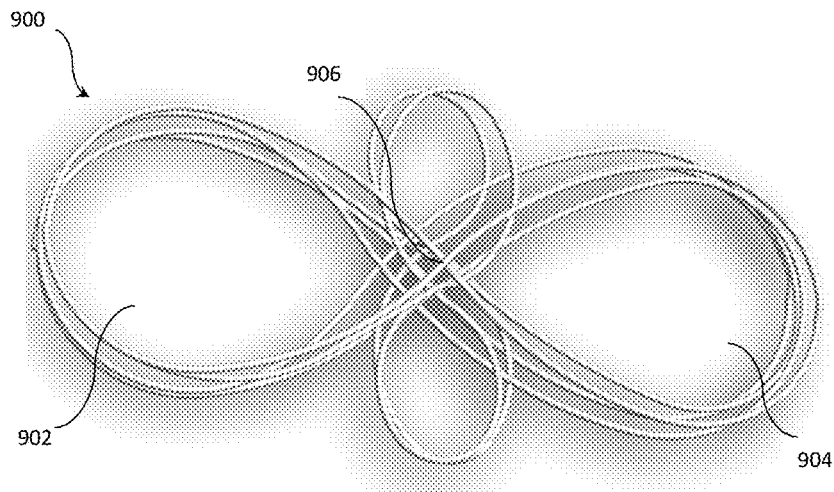
FIG. 9A is a schematic top view of an embolic device forming perpendicular infinity shape portions, according to one embodiment of the invention.
Figure 9B:
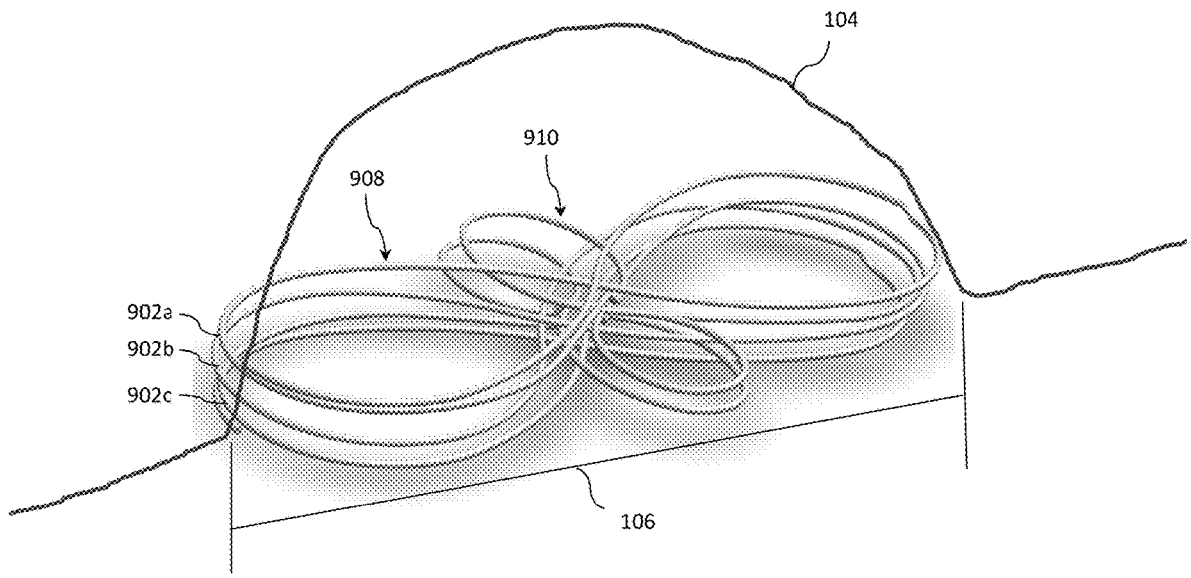
FIG. 9B is a schematic perspective view of an embolic device forming perpendicular infinity shape portions dispersed within an aneurysm, according to one embodiment of the invention.
Figure 9C:
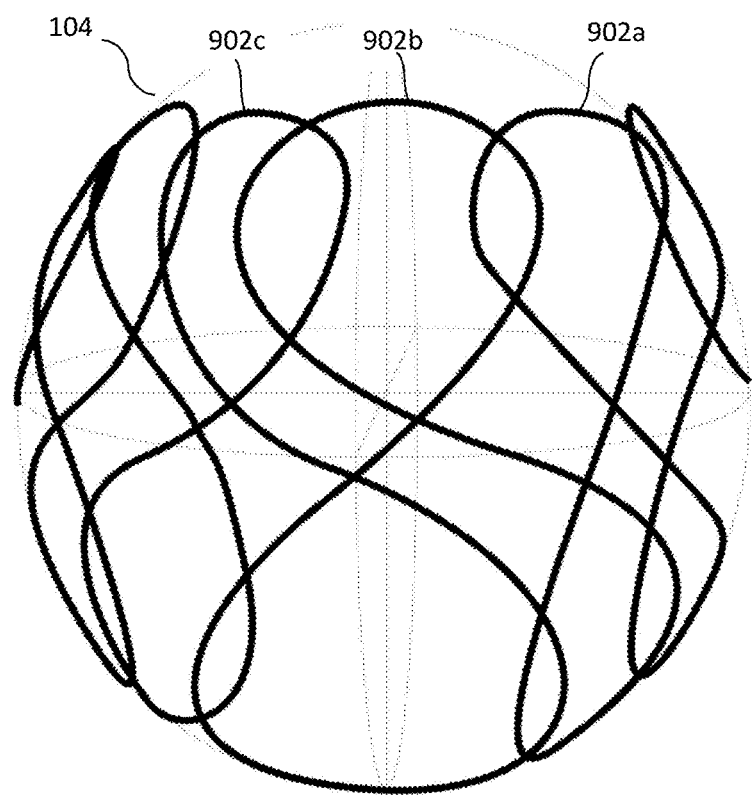
FIG. 9C is a schematic perspective view of an embolic device forming multiple infinity shape portions arranged about the internal perimeter of an aneurysm, according to one embodiment of the invention.

In various embodiments, the aneurysm 104 can be treated by an embolic device shaped to form at least one infinity shape portion, as shown for example in FIGS. 9A-9C. As used herein, the term infinity shape refers to any shape formed by two loops (e.g., loops 902, 904) that cross at a common point (e.g., point 906), e.g., a figure eight shape, a lemniscate shape, etc. Notwithstanding any particular geometric or mathematic usages of the term infinity shape in other contexts, as defined herein, the two loops formed by the infinity shape can be of different sizes or the same size. In some instances, the embolic device 900 can include multiple infinity shape portions 902*a*, 902*b*, 902*c* (see FIG. 9B) stacked on top of each other, e.g., arranged to align with and overlay each other, or in some cases arranged circumferentially about an inner perimeter of the aneurysm (see FIG. 9C). In some instances, the embolic device 900 can include a first group of infinity shape portions 908 (which can include one or more infinity shape portions) arranged along a first axis and a second group of infinity shape portions 910 (which can include one or more infinity shape portions) rotated to be arranged at some angle (e.g., about 15°, about 30°, about 45°, about 60°, about 75°, and about 90°) with respect to the first axis. For example, the second group of infinity shape portions can be arranged substantially perpendicular to the first axis. Although both FIGS. 9A and 9B show infinity shape portions arranged substantially perpendicular to each other, in some instances, all of the infinity shape portions can be arranged along the same axis, e.g., aligned with each other. In other instances, only a single infinity shape portion is formed. Further, although in some instances the infinity shape portions block the neck 106 of the aneurysm, in other instances the infinity shape portion can be located in other portions of the aneurysm. For example, as shown in FIG. 9C, the embolic device can form a series of infinity shape portions that, following deployment, can be arranged circumferentially about the interior perimeter of an aneurysm or other vascular disorder. Such an arrangement can contribute to framing the aneurysm. The infinity shape portions can also be arranged in other patterns. In general, any pattern can be used, including random patterns. Within such patterns, each infinity shape portion can be arranged at any rotational orientation and with any desirable overlap with respect to another infinity shape portion.

In various embodiments, multiple embolic devices can be joined with an interconnect element. The inventors have identified that when the portion of the device that fills the interior of the aneurysm cavity moves (e.g., to expand into apposition with an interior wall of the cavity) it can cause the portion of the device blocking the aneurysm neck to also move or shift, which can impact the effectiveness of the device in blocking the neck.

Figure 10:
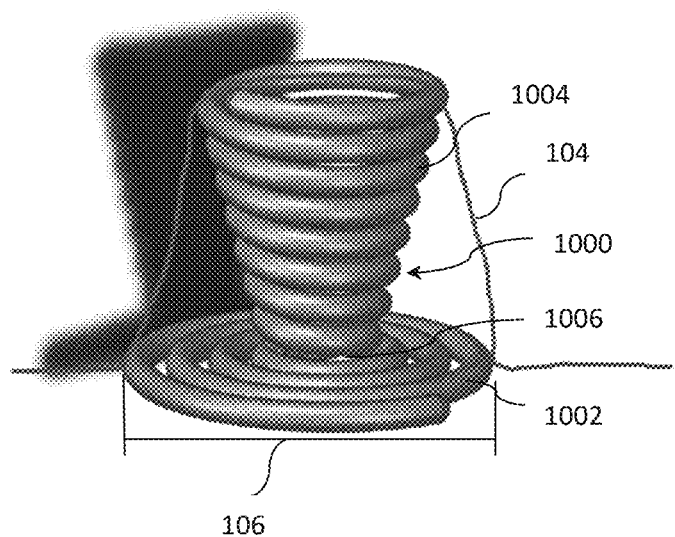
FIG. 10 is a schematic perspective view of a multi-stage embolic device including two embolic devices joined by an interconnect element, according to one embodiment of the invention.

As a solution to this and other problems, embodiments of the present invention include a multi-stage embolic device that includes at least two embolic devices joined by an interconnect element that permits independent freedom of motion and/or relative positioning of each embolic device while they remain joined together. As shown for example in FIG. 10, the multi-stage embolic device 1000 can include a first embolic device 1002 and a second embolic device 1004. In some instances, the first embolic device 1002 is different from the second embolic device 1004. As used herein, the first embolic device 1002 being different from the second embolic device 1004 means that they are two separate devices and not separate portions of a single device of unitary construction or monolithic construction. The first embolic device 1002 being different from the second embolic device 1004 means that the first embolic device 1002 is of non-unitary construction (or non-monolithic construction) with the second embolic device 1004. Said another way, the first embolic device 1002 is not integrally formed with the second embolic device 1004. The first embolic device 1002 being different from the second embolic device 1004 does not require that the devices 1002, 1004 have any other differences, although, in various instances, the devices 1002, 1004 can have other differences. For example, the first and second embolic devices 1002, 1004 can have the same or different dimensions (length, inner diameter, outer diameter, etc.), the same or different stiffness, the same or different porosity, etc. In general, the first embolic device can take any form; for example, the first embolic device 1002 can be a framing device that blocks the neck of the aneurysm. In various instances, the first embolic device 1002 can form any of the particular shapes described above, e.g., a spiral shape, an infinity shape, etc. In general, the second embolic device 1004 can also take any form; for example, the second embolic device 1004 can be a filling device that fills the interior cavity of the aneurysm. In various instances, the second embolic device 1004 can form any of the particular shapes described above, e.g., spiral shape, an infinity shape, etc., or it can take a random or non-geometric shape. In various embodiments, the first embolic device 1002 and the second embolic device 1004 can be located at any location within or around the aneurysm 104, not just the locations shown in FIG. 10.

In general, an interconnect element 1006 joins the embolic devices 1002, 1004 and can include any structure that permits independent freedom of motion and/or relative positioning of each embolic device while they remain joined together. As used herein, independent freedom of motion means that the only constraint on the motion between the embolic devices is that they remain coupled. In various instances, any movement about a coupling point is possible. As a result, motion of the second embolic device 1004 within the aneurysm cavity does not necessarily result in a corresponding motion of the first embolic device 1002 blocking the neck of the aneurysm. In some instances, permitting this freedom of motion represents an advantage of using an interconnect element to join two embolic devices, as opposed to using separate portions of a single coil (or other device) of unitary construction. While the separate portions of a single coil (or other device) may have some independence, they are generally more constrained due to the manufacturing realities of manufacturing a coil (or other device) of unitary construction. In contrast, in some instances, joining two different embolic devices with an interconnect element can afford much greater freedom of motion between the devices. In general, the interconnect element 1006 can be located at any location within or around the aneurysm, depending on where it is advantageous to have independent freedom of motion between the devices, not just the location shown in FIG. 10.

As a few non-limiting examples, the interconnect element can include two linked loops, a nitinol coil (in some cases covering another interconnect element, and in other cases by itself), a hook and loop scheme, a hinge, a suture element, a hole and loop, a ball and socket scheme, a pivot joint, a ball and pivot joint, a universal joint, a saddle joint, any mechanical articulating joint with one or more degrees of freedom, or combinations thereof. In some instances, the interconnect element 1006 can be formed from certain portions of the first embolic device 1002 and the second embolic device 1004. For example, one component of the interconnect element 1006 can be a loop formed at a distal or proximal end of the first embolic device 1002 (e.g., of unitary construction or integral with the first embolic device 1002) and another component of the interconnect element 1006 can be a loop formed at a distal or proximal end of the second embolic device 1004 (e.g., of unitary construction or integral with the second embolic device 1004). In other instances, the interconnect element 1006 is not of unitary construction or integral with either the first embolic device 1002 or the second embolic device 1004 (i.e., the interconnect element is of non-unitary construction or of non-monolithic construction or non-integral with each of the first and second embolic devices 1002, 1004) and is, instead, fastened, adhered, and/or attached to the first and second embolic devices 1002, 1004. In other instances, the interconnect element 1006 is of unitary construction or integral with one of the first and second embolic devices 1002, 1004, and of non-unitary construction or of non-monolithic construction or non-integral with the other embolic device. In various embodiments, regardless of the particular structure employed, two of the first embolic device 1002, the second embolic device 1004, and the interconnect element 1006 are of non-unitary construction with each other.

Figure 11A:
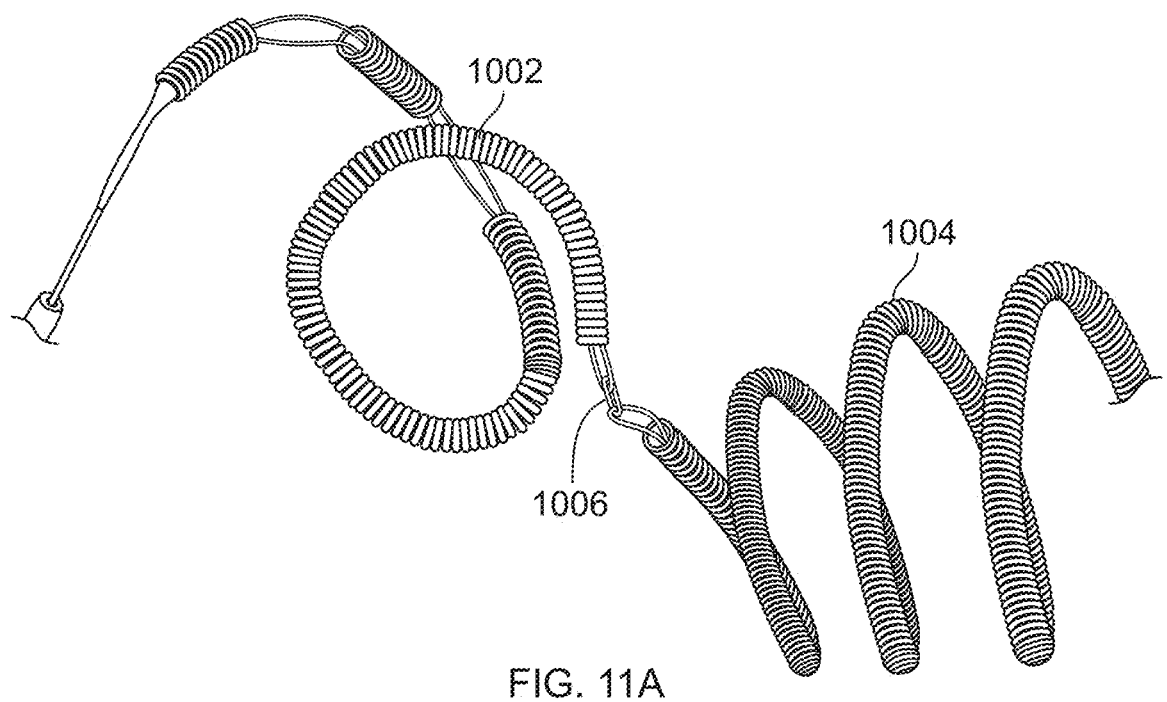
FIGS. 11A-C are pictures showing an interconnect element joining two embolic devices, according to one embodiment of the invention.
Figure 11B:
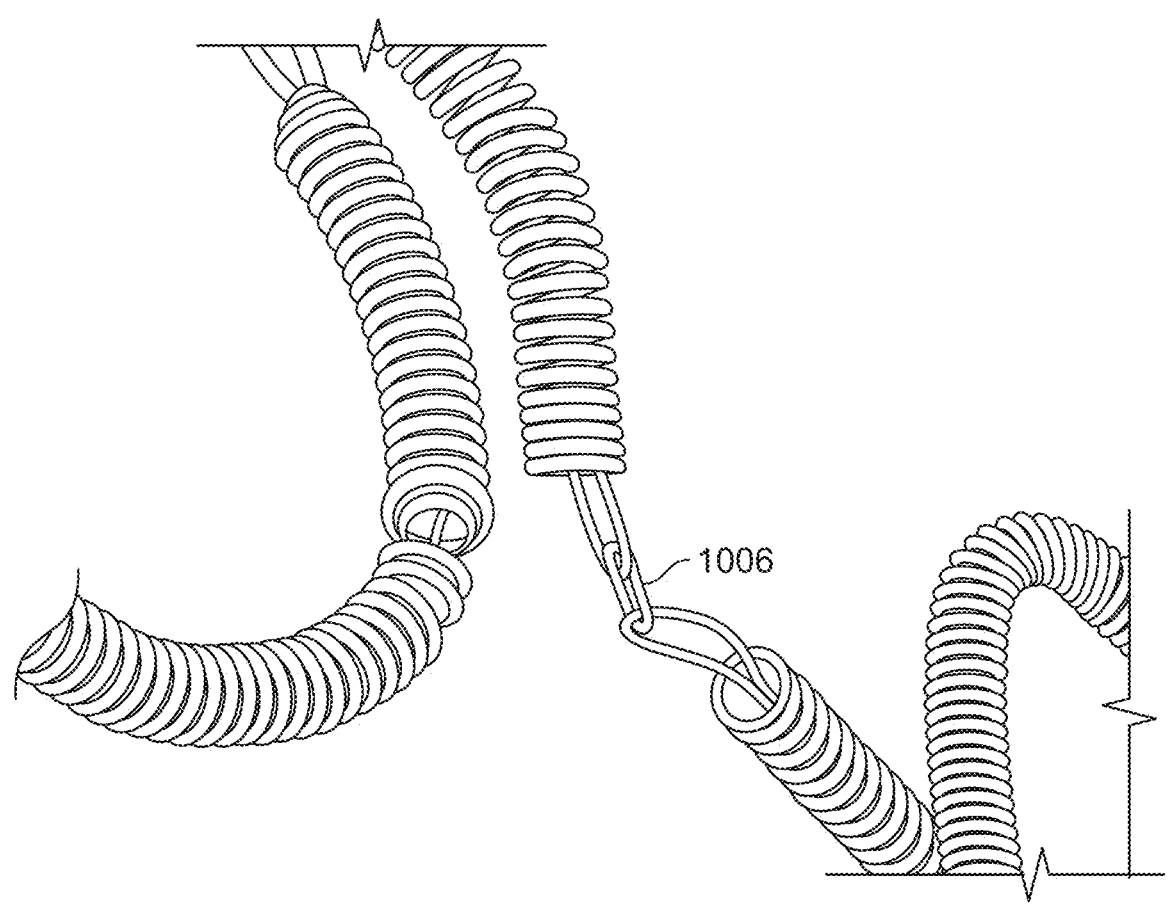
Figure 11C:
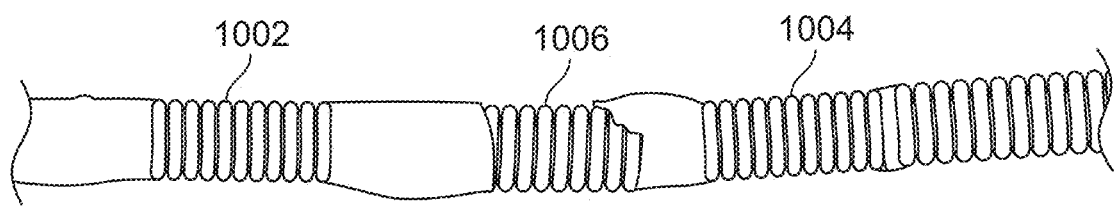

FIGS. 11A-C are pictures showing different views of example interconnect elements 1006. FIGS. 11A-B depict an example interconnect element 1006 formed from two linked loops. FIG. 11C depicts an example interconnect element 1006 formed from two linked loops covered by a nitinol coil (e.g., a different coil than the first and second embolic devices 1002, 1004). In some embodiments, the interconnect element 1006 can include a nitinol coil by itself not covering another interconnect element. As shown in FIG. 11C, in some instances in which the interconnect element 1006 includes a nitinol coil, the nitinol coil is adhered to the first and second embolic devices 1002, 1004. In general, the nitinol coil (or any other interconnect structure adhered to one or both of the embolic devices 1002, 1004) can be adhered to one or both of the embolic devices 1002, 1004 using any known technique. In some implementations, a desirable adhesion technique features adequate material biocompatibility and strength, while minimizing the length required to produce end-to-end fixation between the interconnect element 1006 and the embolic devices 1002, 1004 (which, in some cases, create lengths of unwanted stiffness). As one example, a solder (e.g., gold, silver, or other desirable solder material) can be used to adhere the nitinol coil interconnect element 1006 to the embolic devices 1002, 1004. Other example adhesion techniques include (but are not limited to) use of adhesives, welding (e.g., laser, arc, spot), brazing, diffusion bonding, etc.

Figure 12:
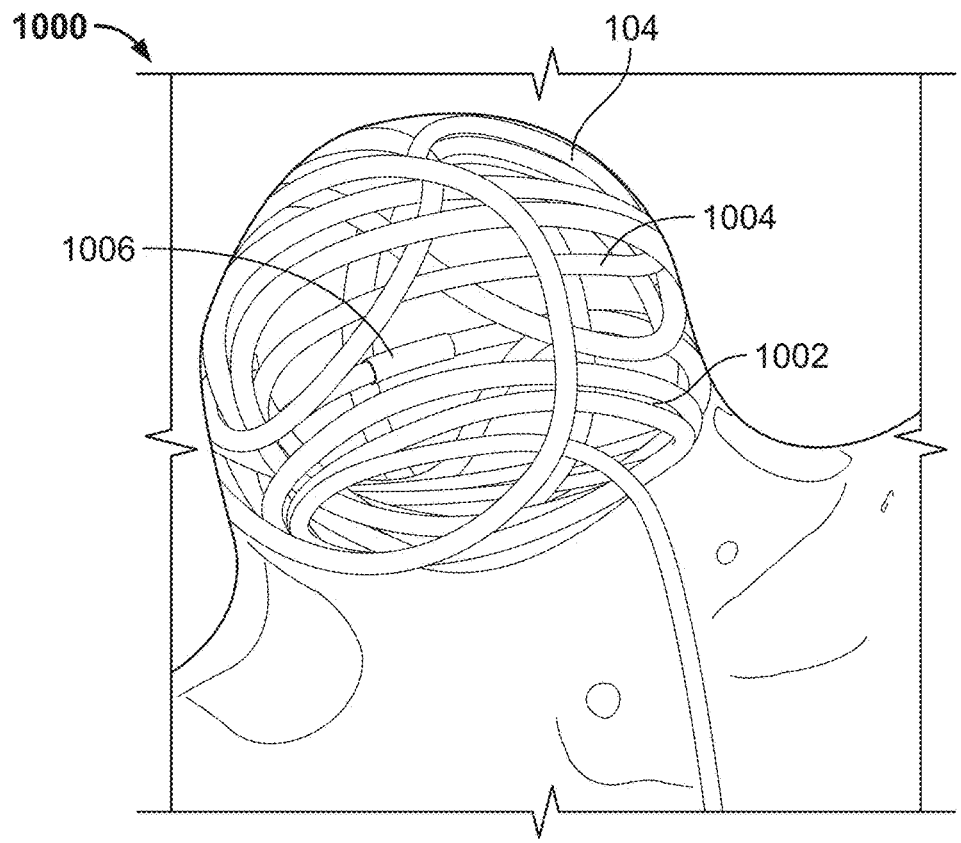
FIG. 12 is a picture showing a multi-stage embolic device deployed within a model aneurysm, according to one embodiment of the invention.

FIG. 12 is a picture showing an example multi-stage embolic device 1000 delivered within a model aneurysm 104. In certain instances, the interconnect element 1006 joins two elements that are delivered to the vascular disorder and intended to remain at the vascular disorder for a treatment period beyond the delivery. In such instances, the interconnect element 1006 does not join an embolic device to a device used for delivering the embolic device to the vascular disorder (e.g., a microcatheter or a delivery pusher).

Figure 13:
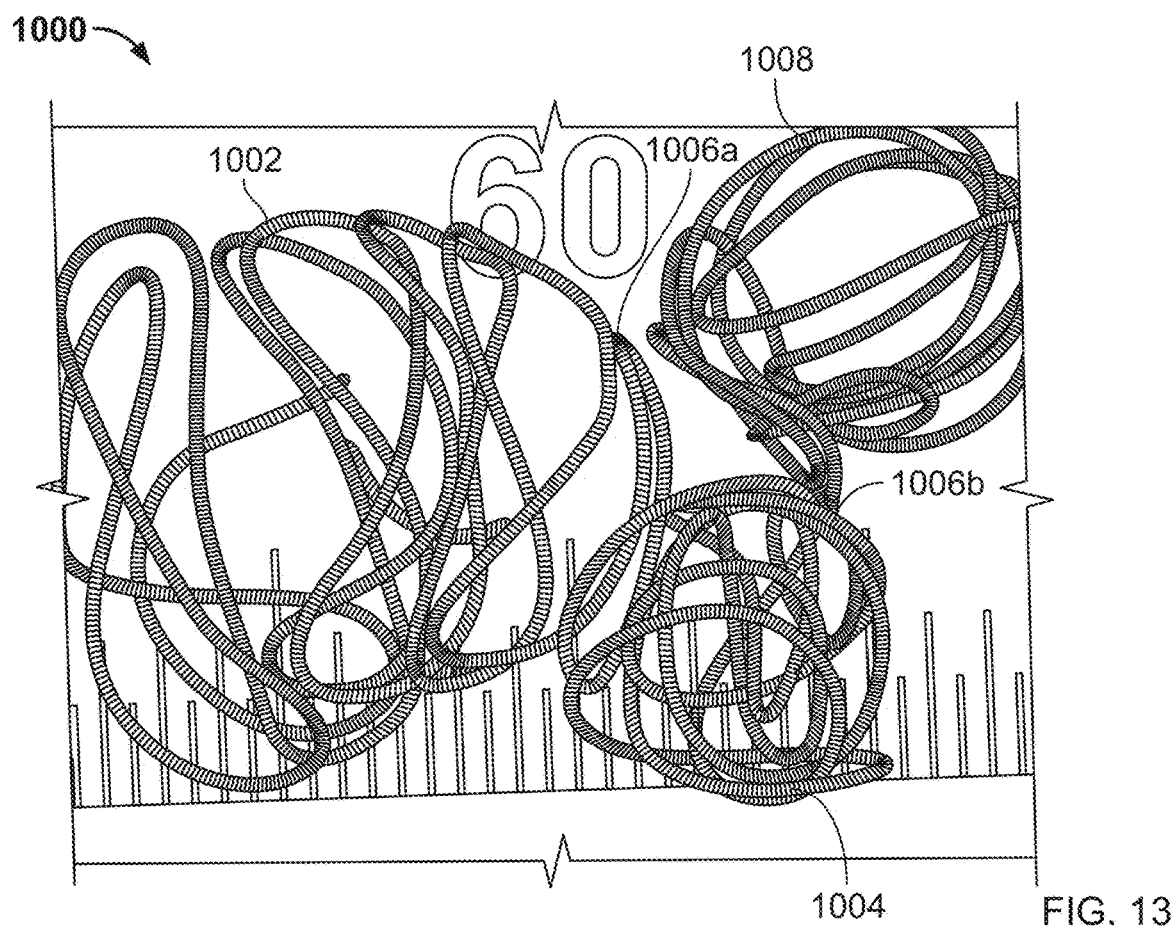
FIG. 13 is a picture showing three embolic devices joined by two interconnect elements, according to one embodiment of the invention.

In various embodiments, more than two embolic devices can be joined together, for example, in parallel using more than one interconnect element. Alternatively, more than two embolic devices can be joined together in series using more than one interconnect element (e.g., up to one less than the number of embolic devices). Combinations of series and parallel arrangements are also contemplated. In general, any number of embolic devices can be joined, e.g., 2, 3, 4, 5, 10, etc. As shown in FIG. 13, the embolic device 1000 can include a first embolic device 1002 joined in series to a second embolic device 1004 with a first interconnect element 1006*a* and the second embolic device 1004 joined in series to a third embolic device 1008 with a second interconnect element 1006*b*. In general, the third embolic device 1008 can take any form (as can any additional embolic device). For example, the third embolic device 1008 can be a finishing device that further fills the interior cavity of the aneurysm. In various instances, the third embolic device 1008 (and any additional embolic device) can form any of the particular shapes described above, e.g., spiral shape, infinity shape, etc., or it can take a random or non-geometric shape. The third embolic device 1008 (and any additional embolic device) can be located in an any location within or around the aneurysm.

In various embodiments, each of the embolic devices (e.g., 1002, 1004, 1008) of the multi-stage embolic device 1000 can have different properties and behave differently from each other. In general, any embolic device property can be variable amongst the embolic devices. For example, some or all of the embolic devices can have different sizes, shapes, lengths, stiffness, porosity, etc. In other instances, some of all of the embolic devices can have the same of some or all properties. This customizable and independent nature of the embolic device properties can enable operators (e.g., physicians) greater freedom to shape and control coil deployment and positioning than with conventional devices. As one example, an operator can deliver a coil such that it is initially positioned in a first direction and then pivots to be positioned in a different direction at an angle (e.g., 15°, 30°, 45°, 60°, 75°, 90°, etc.) to the first direction.

As mentioned above, in various embodiments, the embolic devices described herein can include a structure (e.g., microcoil, flat sheet, thin film, etc.) covered by a cover element or not covered by a cover element. With reference to the multi-stage embolic device 1000, in various embodiments, any, none, or all of the individual embolic devices (e.g., 1002, 1004, 1008, etc.) can be covered or not covered by a cover element.

Unless expressly described elsewhere in this application (e.g., the use of the word "substantially" with respect to a geometric shape), as used herein, when the term "substantially" or "about" is before a quantitative value, the present disclosure also includes the specific quantitative value itself, as well as a ±10% variation from the nominal value unless otherwise indicated or inferred.

Having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. A multi-stage embolic device for use in treating a vascular disorder, the multi-stage embolic device comprising:
    a first embolic device;
    a second embolic device different from the first embolic device;
    a hook and loop interconnect element joining the first and second embolic devices permitting independent freedom of motion between the first and second embolic devices while remaining joined together, such that the only constraint on the motion between the first and second embolic devices is that they remain joined; and
    a coil disposed over the hook and loop interconnect element and adhered to the first embolic device and the second embolic device,
    wherein at least one of the first embolic device and the second embolic device comprises a series of alternating narrow portions and link portions, and
    wherein each of the first embolic device and the second embolic device comprises at least one of a coil, a flat sheet, a thin film, and combinations thereof.

2. The embolic device of claim 1, wherein at least one of the first embolic device and the second embolic device comprises a material selected from the group consisting of platinum, nitinol, alloys thereof, and combinations thereof.

3. The embolic device of claim 1, wherein at least one of the first embolic device and the second embolic device comprises a thickness in a range from 0.0005 inches to 0.027 inches.

4. The embolic device of claim 1, wherein at least a portion of the embolic device is radiopaque.

5. The embolic device of claim 1, wherein at least one of the first embolic device and the second embolic device comprises a flexible structure comprising a series of alternating narrow portions and link portions, wherein each narrow portion is fixedly attached to proximate link portions and further comprising:
    a strain relief element between each narrow portion and the proximate link portions.

6. The embolic device of claim 5, wherein the strain relief element is formed from at least one of a melted suture material and a melted polymer.

7. The embolic device of claim 1, wherein at least one of the first embolic device and the second embolic device comprises a flexible structure comprising a series of alternating narrow portions and link portions, wherein each link portion comprises a diamond-like shape.

8. The embolic device of claim 1, wherein at least one of the first embolic device and the second embolic device comprises a flexible structure comprising a series of alternating narrow portions and link portions, wherein each link portion is adapted to compress when the embolic device is disposed within a microcatheter.

9. The embolic device of claim 8, wherein each link portion is further adapted to expand upon the deployment of the embolic device from the microcatheter.

10. The embolic device of claim 1, wherein at least one of the first embolic device and the second embolic device comprises a flexible structure comprising a series of alternating narrow portions and link portions, wherein the narrow portions and the link portions alternate with consistent spacing.

11. The embolic device of claim 1, wherein at least one of the first embolic device and the second embolic device comprises a flexible structure comprising a series of alternating narrow portions and link portions, wherein the narrow portions and the link portions alternate with inconsistent spacing.

12. The embolic device of claim 1, wherein the first embolic device and the second embolic device are attached in series.

* * * * *